United States Patent [19]

Montefiori

[11] Patent Number: 5,057,325

[45] Date of Patent: Oct. 15, 1991

[54] METHOD OF INHIBITING REPLICATION OF HIV WITH WATER-SOLUBLE MELANINS

[75] Inventor: David C. Montefiori, Nashville, Tenn.

[73] Assignee: Vanderbilt University, Nashville, Tenn.

[21] Appl. No.: 496,241

[22] Filed: Mar. 20, 1990

[51] Int. Cl.[5] ............... A01N 37/18; A61K 37/02
[52] U.S. Cl. ............................ 424/522; 514/2; 514/885
[58] Field of Search ............... 424/520, 522; 514/2, 514/885

[56] References Cited

PUBLICATIONS

Blois, "The Melanins: Their Synthesis and Structure", Photochemical and Photobiological Reviews, vol. 3, pp. 115–135, 1978.

Debing et al., "Melanosome Binding and Oxidation-Reduction Properties of Synthetic L-DOPA-Melanin as In Vitro Tests for Drug Toxicity", Molecular Pharmacology, 33: 470–476, Jan. 1988.

*Primary Examiner*—Nathan M. Nutter
*Attorney, Agent, or Firm*—Tilton, Fallon, Lungmus & Chestnut

[57] ABSTRACT

Replication of human immunodeficiency virus (HIV) is inhibited in human patients by administering melanins. L-dopa melanin is preferred, but other water-soluble melanins can be used.

14 Claims, No Drawings

METHOD OF INHIBITING REPLICATION OF HIV WITH WATER-SOLUBLE MELANINS

FIELD OF INVENTION

The general field of this invention is therapeutic agents for combatting viral infections. In particular, however, this invention relates to the treatment of patients infected with a human immunodeficiency virus (HIV) which causes Acquired Immune Deficiency Syndrome (AIDS).

BACKGROUND OF INVENTION

Melanins are heteropolymers derived from the spontaneous polymerization of intermediates formed during the enzymatic or chemical oxidation of L-tyrosine and other phenolic molecules, or the autooxidation of L-dopa and similar catecholes. (See Blois, "The Melanins: Their Synthesis and Structure" in *Photochemical and Photobiological Reviews*, Vol. 3, pages 115-135, 1978; Lerner, *Advances, in Neurology*, 5 211-223, 1974; and Duff, et al., *Biochemistry*, 27::7112-7116, 1988.) Natural melanins occur as pigments in hair, skin, irides of the eye, and substantia nigra and locus ceruleus of the brain. The known biological functions of natural melanins derive from their diverse coloration, their ability to absorb ultraviolet radiation, and their electron transfer properties.

The various colors of melanins depend, in large part, on the initial substrate. Existing terminology follows this approach to classification. Brown and black melanins originating from L-tyrosine and L-dopa are termed "eumelanins", while yellow and red melanins which contain sulfhydryl compounds are termed "pheomelanins" (Prota, 1980, cited above). Eumelanin and pheomelanin biosyntheses occur in specialized organelles of melanocytes called melanosomes (Seiji, M., et al., *Nature (London)* 197:1082-1084, 1963), and they become water-insoluble melanin granules.

Neuromelanins are found in the cytoplasm of catecholamine-producing neurons (Bazelton, M., et al., *Neurol* 17:512-519, 1967), and can be synthesized from L-dopa, dopamine, norepinephrine, epinephrine, and 5-hydroxytryptamine (Blois, 1978, and Lerner, 1974, both cited above). In the brain the neuromelanins primarily are present in water-insoluble forms.

The melanins of particular interest for the purpose of this invention are water-soluble forms of eumelanins, neuromelanins and pheomelanins. These forms of melanins can be prepared from known starting materials such as L-dopa, L-tyrosine, etc. (See Arnow, *Science*, 87:308, 1938; and Debing, et al., *Molecular Pharm.*, 33:470-476, 1988.)

Melanins are also known to bind certain chloroquine and phenothiazine antibiotics, which may account for the toxicity of these antibiotics in tissues with high melanin content (Lindquist, N.G., *Upsala J. Med. Sci.* 91:283-288, 1986; and Larsson, et al., *Biochem. Pharmacol.* 28:1181-1187, 1979). Electrostatic forces involving anionic sites on melanins presumably carboxyl groups) appear to be important to the antibiotic affinity of melanins (Larsson, et al., cited above). As far as is known, however, there have been no reports of melanins displaying any antiviral or antibacterial activity.

Human immunodeficiency virus (HIV) is the etiologic agent of Acquired Immune Deficiency Syndrome (AIDS). This lentivirus infects CD4+cells causing their direct or indirect destruction (Lifsun, et al., *Science* 232:1123-1127, 1986); Siliciano, et al., *Cell* 54:561-575, 1988). As a consequence of CD4+cell depletion, the host becomes susceptible to opportunistic infections and neoplasms. Several drugs have been identified which inhibit the replication of this virus in vitro (Haseltine, W.A., *J. Acquir. Immune Def. Syndr.*, 2:311-324, 1989) but only 3'-azidothymidine (AZT) has received general acceptance for clinical use. The proven clinical efficacy of AZT is limited, and its use is restricted by toxicity and drug-resistant forms of the virus. Therefore, new antiviral agents are urgently needed.

The problem of treating patients infected with human immunodeficiency virus is that the viruses which cause AIDS have serological subtypes. The most prevalent form of HIV is designated HIV-1, and a less prevalent subgroup is HIV-2. (Popovic, et al., *Science* 224:497-500, 1984; Hahn, et al., *PNAS* 82:4813-4817, 1985; and Clavel, et al., *Nature* 324: 691-695, 1986.) It is desired to find an agent which is effective for controlling or inhibiting all forms of HIV.

SUMMARY OF INVENTION

This invention is based on the discovery that a related group of melanins including the eumelanins, neuromelanins, and the pheomelanins when prepared in water-soluble form, are capable of inhibiting the replication and pathogenesis of the viruses which cause AIDS (e.g., AIDS-viruses), including both the HIV-1 and HIV-2 viral subtypes. During the experimental work on this invention, it was demonstrated in vitro that these water-soluble melanins can completely or partially protect human lymphocytes from infection by cell-free AIDS-viruses. This protective action is strongly positive at lower concentrations, but also significant for HIV-2 at a higher concentration. It was further demonstrated in vitro that the water-soluble melanins interfere with the fusion of AIDS-virusinfected cells with uninfected cells, thus retarding cytopathic effects of the viruses and cell-to-cell spread of the viruses. These results identify a new biological activity of water-soluble melanins as antiviral compounds active against the family of AIDS-viruses. This is believed to be a completely novel and unobvious therapy. As far as is known, no melanin in any form has been proposed for use as a therapeutic agent.

DETAILED DESCRIPTION

The melanins which are useful as antiHIV agents for practicing the therapeutic method of this invention are water-soluble forms of melanins prepared from known starting materials. These starting materials include the following: L-dopa, L-dopa/cysteine, L-dopa/glutathione, L-tyrosine, serotonin (5-hydroxytryptamine), dopamine (3-hydroxytyramine), adrenalin (epinephrine), and noradrenalin (norepinephrine). For purposes of this invention, melanins from these starting materials are prepared and maintained in water-soluble form. The water-soluble melanins exhibit pigment properties, the predominant colors being black or brown. In relation to existing melanin classification, the melanins of this invention include water-soluble forms of eumelanins, neuromelanins, and pheomelanins. Most if not all of these water-soluble melanins include a benzene ring with two hydroxyl groups in ortho position, and an aromatic indole or aliphatic amine group. They are water-soluble heteropolymers which are prepared by spontaneous or induced oxidation of the starting materials.

Preferred starting materials are L-dopa and L-tyrosine. For commercial purposes, L-dopa is believed to be the most desirable. The water-soluble melanins prepared from the preferred starting materials can be referred to as L-dopa melanin or L-tyrosine melanin. L-tyrosine melanin can be purchased from the Sigma Chemical Co., St. Louis, MO. Melanins prepared from other starting materials can be respectively designated serotonin melanin, dopamine melanin, adrenalin melanin, and noradrenalin melanin. Pheomelanins can be prepared from a mixture of L-dopa with cysteine or glutathione. The resulting water-soluble melanins may be as L-dopa/cysteine melanin or L-dopa/glutathione melanin, and differ from eumelanins and neuromelanins by containing sulfur.

Most of the water-soluble melanins for use in practicing the method of the present invention are not known to be commercially available. However, they can be readily prepared from commercially available starting materials. The starting materials referred to above are all available commercially in the United States, viz. from Sigma Chemical Company, St. Louis, MO. The starting materials for substrates are water-soluble and are dissolved to form dilute aqueous solutions. The solution is made mildly alkaline with an alkaline reagent such as sodium hydroxide, and oxidation can be promoted by introducing oxygen or air into the solution. For example, air can be bubbled through an alkaline solution of the substrate at ordinary room temperatures (20-25° C.) to promote the oxidation of the substrate to form the melanins.

Formation of the melanins can be detected by a change of color in the solution, the melanin pigment usually being observed as a black or brown color in the solution. Prototype preparatory procedures for L-dopa melanin have been described in the literature: Arnow, *Science*, 87:308 (1938) and Debing, et al., *Molecular Pharm.*, 33:470-476 (1988). The procedures of these references for preparing L-dopa melanin are suitable for use with the other starting materials referred to above.

After the melanins have been prepared in the alkaline aqueous solution, they can be recovered by precipitation under acid condition, such as by adding hydrochloric acid. The precipitate can be collected by centrifugation or filtration, and redissolved in water or an aqueous buffer solution. Precipitation of redissolved melanins can be repeated to improve purity. If a product is desired in dry form, it can be lyophilized.

The water-soluble melanins of this invention act within the circulatory system. They are believed to act by inhibiting the infection of T lymphocytes which have CD4 receptors. However, the exact mechanism by which the melanins inhibit the replication of HIV in vivo has not been established. It seems probable, though, that the melanins interfere with the binding of the gp120 envelope protein of the virus to the CD4 receptors of the T lymphocytes.

Water-soluble melanins of this invention are believed to be relatively non-toxic, so that they can be safely used in vivo at effective concentrations and for long periods of administration. The melanins can be administered orally or parenterally. For convenience of long-term administration of non-hospitalized patients, it is believed that oral administration will be preferred. When the patient is hospitalized, the melanins can be introduced as a component of a parenteral solution, such as a normal saline or glucose solution. Whether administered orally or parenterally, it is believed that the amount of water-soluble melanin to obtain at least partial inhibition of the replication of HIV is from about 50 to 200 milligrams (dry basis) per 24 hours. Based on present information, preferred dosages can range from about 50 to 200 milligrams (dry basis) per 24 hours. For oral administration, liophilized water-soluble forms of the melanins may be tabletted. To facilitate preparation of tablets, the melanins may be combined with a carrier such as lactose. For maximum absorption, tabletted melanin may be coated with an enteric covering to permit passage through the stomach into the intestine before dissolution. For intravenous solutions, concentrations of up to 0.2 milligrams per milliliter of solution can be used, such as a concentration of 50 to 200 milligrams of the melanin per liter of solution. Also, if desired, sterile aqueous solutions, such as normal saline solutions of the melanin, can be used for intramuscular or subcutaneous injection.

The activity of the melanins for inhibiting replication of HIV can be confirmed by known assays, including particularly the assay described by Montefiori, et al., *J. Clin. Microb.*, 26:231-235, 1988. That assay utilizes human T-cell lymphotropic virus type I-immortalized MT-2 cells as targets for infection. Cytolysis can be quantitated by vital dye uptake of poly-L-lysine-adhered cells as an endpoint for infection. The MT-cell assay has now been accepted as a standard screening test.

As determined by the MT-2 cell assay, effective in vitro inhibition levels are in the range from about 0.2 to 10 micrograms ($\mu$g) per milliliter of solution. It is believed that effective in vivo levels will be similar. For example, desirable in vivo levels of melanin in the blood are from about 1 to 10 micrograms ($\mu$g) per milliliter of serum.

The melanin treatments of this invention can be used with any patients infected with the HIV, including particularly viruses of the serological type HIV-1 but also including patients infected with other HIVs such as HIV-2. The treatment may be commenced with pre-AIDS apparently healthy persons infected with the virus. Persons manifesting the lymphadenopathy syndrome, or AIDS-Related Complex, may also be treated. Further, it is believed that the treatment will be of value for patients diagnosed as having AIDS. Preferably, however, it is believed that the treatment will be used with patients who have not progressed to active AIDS disease.

The effectiveness of the treatment can be monitored by known procedures and observations. For example, such procedures and observations were recently described: *ASM News*, Current Topics, 55: 586-588, 1989. A laboratory test marker was recommended which involves observation of the level in the blood of CD4-bearing T lymphocyte cells. In patients that have the AIDS disease, the most direct criteria rest on clinical observations, such as reduced incidents of opportunistic infections and extended lifespans. Other laboratory measures include tests for the p24 antigen of HIV, or additional components of the immune system including beta-2-microglobulin and/or neopterin. The criteria selected may depend on the stage of the HIV infection. For pre-AIDS patients, the quantity of HIV antigens detected in the blood may be the best measure. For example, Coulter Immunology Division of Coulter Corportion provides an HIV Ag Assay which can be used. This is an enzyme immunoassay using a murine monoclonal antibody (anti-HIV core antigen) coated onto microwell strips. The assay detects HIV antigens in plasma or serum.

The scientific basis of the present invention is further elucidated by the following Experimental Examples.

EXAMPLE I

Synthesis of Water-Soluble Melanins

L-dopa melanin was synthesized in watersoluble form essentially as described previously (Arnow, Science, 87:308, 1938). One gram of L-dopa (Sigma Chemical Company, St. Louis, MO) was dissolved in 400 ml of 0.025N NaOH and incubated for 2 days at room temperature with constant aeration. Aeration was accomplished with the aid of an air sparger using air that had been passed through a solution of 1N NaOH. Melanin was precipitated from the dark brown solution by adding 2 ml of concentrated HCl. The moist precipitate was collected by centrifugation, dissolved in 400 ml of deionized water, and precipitated again with 1 ml of concentrated HCl. The melanin was purified this way a total of four times, and then dissolved in 20 ml of 0.025 NaOH (the solution had a neutral pH at this time) and lyophylized. The final yield was 100 mg of a fine black powder which was soluble in phosphate buffered saline (PBS), pH 7.4, to at least 500 mg/ml.

Dopamine, serotonin and norepinephrine melanins were synthesized as described above for L-dopa melanin except that dopamine, serotonin and norepinephrine were substituted for L-dopa, respectively. L-dopa/glutathione melanin was synthesized as described above for L-dopa melanin except that 0.5 gm of L-dopa and 0.5 gm of glutathione were used (glutathione was dissolved first). L-dopa/L-cysteine melanin was synthesized as described above for L-dopa melanin except that 0.5 gm of L-dopa and 0.5 gm of L-cysteine were used (L-cysteine was dissolved first). L-tyrosine melanin (obtained by hydrogen peroxide oxidation of L-tyrosine) was purchased from Sigma Chemical Company (St. Louis, MO) and was soluble at 0.2 mg/ml in PBS.

EXAMPLE II

Protection of MT-2 Human Lymphoblastoid Cells from HIV-1 and HIV-2 Cytopathic Infection Antiviral activities of the synthetic water-soluble melanins derived as described in Example I from L-tyrosine, L-dopa, dopamine, serotonin, norepinephrine, L-dopa/glutathione, and L-dopa/ L-cysteine were measured in 96well microdilution plates as described ( Montefiori, et al., *J. Clin. Microbiol.* 26:231-235, 1988). Briefly, 2-fold serial dilutions of melanins were made in triplicate in a total of 100 ul growth medium (RPMI-1640 containing 12% heat-inactivated fetal bovine serum and 50 ug gentamicin/ml) per well. MT-2 cells ($5 \times 10^4$) in 100 ul of growth medium were added to each well and incubated for 10 minutes. Fifty microliters of virus ($5 \times 10^4$ TCID$_{50}$/50 ul) were then added to all wells except for 1 row of eight non-cytopathic control wells; these received growth medium in place of virus. Viral-induced cytopathic effect (CPE) was quantitated 3 days later by vital dye (neutral red) uptake in remaining viable cells. Neutral red uptake is a linear function of cell viability with A$_{540}$ of 0.025 to 0.85 corresponding to $2 \times 10^4$ to $25 \times 10^4$ viable cells/well (Montefiori, et al., *J. Clin. Microbiol.* 26:231-235, 1988). Percent protection is defined as the difference in A$_{540}$ between test wells (cells +melanin +virus) and virus control wells (cells +virus) divided by the difrence in A$_{540}$ between cell control wells (cells only) and virus control wells.

L-tyrosine and L-dopa melanins protected MT-2 cells from infection by cell-free virus as indicated by dramatic reductions in viral-induced cytopathic effects as shown by the data of Table A. Representatives of the two predominant genetic and serological types of HIV (i.e., HIV-1 and HIV-2; Popovic, M., et al., *Science* 224:497-500, 1984; , Hahn, B.H., et al., *PNAS* 82:4813-4817, 1985; Clavel, F, et al., *Nature* 324:691-695, 1986) were used in these experiments. Antiviral activity was strongest against the HTLV-III$_B$ and HTLV-III$_{RF}$ isolates of HIV-1. These two isolates are serologically indistinguishable but genetically diverse. Most potent activity was that of L-dopa melanin, which at 0.31-10 µg/ml provided 100% protection against HTLV-III$_B$, and at 0.62-10 µg/ml provided 100% protection against HTLV-III$_{RF}$. Effective doses that provided 50% protection (ED$_{50}$) against HTLV-III$^B$ and HTLV-III$_{RF}$, respectively, were 0.3 and 0.2 µg/ml for L-tyrosine melanin, and 0.2 and 0.4 µg/ml for L-dopa melanin. Both melanins were less active against the serologically and genetically diverse HIV-2 isolate, HIV-2$_{ROD}$.

Here, the ED$_{50}$ was 1.5 µg/ml for L-tyrosine melanin and 3 µg/ml for L-dopa melanin. Melanin concentrations greater than 10 mg/µl were toxic to the cells when measured by vital dye uptake as described (Montefiori, et al., *J. Clin. Microbiol.* 26:231-235, 1988). L-tyrosine and L-dopa at 1-100 µg/ml had no antiviral activity in these assays. Therefore, beginning substrates for melanin synthesis were not responsible for the antiviral activities observed. It is also unlikely that intermediates in melanin biosynthesis were responsible for antiviral activity since these intermediates are highly unstable and short lived (Raper, H.S., *Physiol. Rev.* 8:245-282, 928; Mason, H.S., *J. Biol. Chem.* 172:83-99, 1948; Prota, G., *J. Invest. Dermatol.*, 75:122-127, 1980).

Dopamine, serotonin, norepinephrine, L-dopa/glutathione, and L-dopa/L-cysteine melanins also protected MT-2 cells from infection by cellfree virus as indicated by dramatic reductions in viral-induced cytopathic effects (Table A). Here, the antiviral activity was demonstrated using only the HTLV-III$_B$ isolate of HIV-1. The ED$_{50}$ of these melanins were 0.09 µg/ml for dopamine melanin, 0.15 µg/ml for serotonin melanin, 0.1 µg/ml for nor melanin, 0.25 µg/ml for L-dopa/glutathione melanin, and 0.12 µg/ml for L-dopa/L-cysteine melanin.

TABLE A*

| | µg melanin/ml | | | |
|---|---|---|---|---|
| Melanin (Virus) | 0.08 | 0.16 | 0.31 | 0.62 |
| L-tyrosine (IIIB) | — | 35 | 62 | 72 |
| L-tyrosine (RF) | — | 18 | 72 | 85 |
| L-tyrosine (HIV-2) | — | 0 | 0 | 5 |
| L-Dopa (IIIB) | — | 5 | 100 | 100 |
| L-Dopa (RF) | — | 5 | 15 | 90 |
| L-Dopa (HIV-2) | — | 5 | 6 | 15 |
| Dopamine (IIIB) | 42 | 77 | 79 | 82 |
| Serotonin (IIIB) | 0 | 47 | 82 | 93 |
| Norepinephrine (IIIB) | — | — | 64 | 88 |
| L-Dopa/Glutathione (IIIB) | — | 4 | 66 | 83 |
| L-Dopa/L-Cysteine (IIIB) | 10 | 60 | 87 | 95 |
| Melanin (Virus) | 1.25 | 2.5 | 5 | 10 |
| L-tyrosine (IIIB) | 78 | 95 | 100 | 100 |

TABLE A*-continued

| | μg melanin/ml | | | |
|---|---|---|---|---|
| L-tyrosine (RF) | 100 | 100 | 100 | 100 |
| L-tyrosine (HIV-2) | 30 | 70 | 95 | 85 |
| L-Dopa (IIIB) | 100 | 100 | 100 | 100 |
| L-Dopa (RF) | 100 | 100 | 100 | 97 |
| L-Dopa (HIV-2) | 25 | 42 | 78 | 78 |
| Dopamine (IIIB) | 88 | 93 | 89 | 79 |
| Serotonin (IIIB) | 96 | 92 | 96 | 96 |
| Norepinephrine (IIIB) | 86 | 81 | 87 | 89 |
| L-Dopa/Glutathione (IIIB) | 81 | 97 | 95 | 88 |
| L-Dopa/L-Cysteine (IIIB) | 95 | 94 | 89 | 86 |

*Values in this table are percent protection values from infection assays.

EXAMPLE III

Inhibition of HIV-1 Replication in MT-2 and H9 Lymphoblastoid Cells and PHA-Stimulated T Cells by Melanin MT-2, H9 and phytohemagglutinin (PHA) stimulated T cells ($2-5 \times 10^6$/10 ml growth medium) were challenged for 4 hours with $5 \times 10^6$ TCID$_{50}$ of HIV-1 (HTLV-III$_B$) in the presence and absence of synthetic L-tyrosine or L-dopa melanins (10 μg/ ml). The cells were then washed in growth medium to remove melanin and unadsorbed virus, and incubated in fresh growth medium without melanin Cultures were maintained for 3 days (MT-2), 5 days (H9) or 9 days (PHA-stimulated T cells), then examined by IFA and RT activity for viral antigen synthesis. IFA was performed on air-dried, acetone-methanol fixed cells as described (Montefiori, D.C., and Mitchell, W.M., Virol. 155:726-731, 1986) using serum from an HIV-1-positive individual. This serum was positive by Western immunoblot (E.I. DuPont, Wilmington, DE) for all major HIV-1 antigens. RT activity was measured by the incorporation of methyl [$^3$H]dTTP into poly (rA)·(dT)$_{15}$ template-primer as described (Poiesz, B.J., et al., PNAS 77:7415-7419, 1980). Peripheral blood lymphocytes (PBLs) were isolated from heparinized whole blood using the Sepracell 2-step procedure (Sepratech Corp., Oklahoma City, OK). Residual monocytes were removed by adherence to the surface of a culture flask after which B cells were removed by passage through an immunoaffinity column (T-Cell Column Kit, Beckman Instruments, Inc., Fullerton, CA). The final T cell preparation was greater than 98% T cells as shown by IFA using fluorescein-conjugated anti-leu-f (CD3) and phycoerythrin-conjugated anti-leu-12 (CD19), both from Becton Dickinson (Mountain View, CA). Fluorescence was detected using a Nikon DIAPHOT-TMDEF fluorescence microscope. T cells were stimulated with PHA-P (P-L Biochemicals) at 1 μg/ml for 24 hours, washed with growth medium, and cultured in the presence of recombinant interleukin-2 (rIL-2, E.I. DuPont, 12.5 units/ml final) for the duration of experiments.

Immunofluorescent positive cells and reverse transcriptase (RT) release into culture fluids were greatly reduced in all cultures in the presence of melanin as shown by the data of Table B. Since melanin was present during a 4 hour virus adsorption period only, the site of antiviral activity was probably an early stage in the HIV replication cycle. These results also demonstrate that the antiviral activity of melanin is not cell line specific.

TABLE B

| Cells*[a] | % IFA Positive | | RT Activity (cpm × 10$^{-4}$/ml) | |
|---|---|---|---|---|
| | Exp. 1 | Exp. 2 | Exp. 1 | Exp. 2 |
| MT-2 | 100[b] | 100[b] | 581 | 395 |
| MT-2 + L-tyrosine melanin | 5 | 1 | 45 | 5 |
| MT-2 + L-dopa melanin | 5 | 1 | 11 | 1 |
| H9 | 100 | 100 | 375 | 344 |
| H9 + L-tyrosine melanin | <1 | <1 | 5 | 1 |
| PHA T Cells | 20 | 20 | 52 | 55 |
| PHA T Cells + L-tyrosine melanin | <1 | <1 | 1 | 2 |

[a]Cells were challenged with HTLV-III$_B$ in the presence and absence of melanins at 10 μg/ml as described in "Materials and Methods".
[b]Denotes an abundance of syncytia and the beginning of cytopathic effect.

EXAMPLE IV

Inhibition of HIV-Induced Syncytium Formation by Melanin

Syncytium formation was induced by mixing chronic HIV-infected H9 cells with MT-2 cells in the presence and absence of L-tyrosine or L-dopa melanin in 96-well microdilution plates. Serial dilutions of melanins were made in triplicate MT-2 cells ($1.5 \times 10^5$) in 100 μl of growth medium were then added to each well. HIV-infected H9 cells ($1.5 \times 10^4$) in 50 μl of growth medium were added to all wells except one row of 8 non-cytopathic control wells, which received uninfected H9 cells. Syncytium formation leads to, and is directly proportional to, cytopathic effect in this assay (Montefiori, et al., PNAS 85:9248-9252, 1988). After incubation at 37° C. for 20 hours, syncytium formation was observed microscopically while viable cells were measured by vital dye uptake as described in Example II.

HIV-induced cytopathic effect in cell culture is mainly the result of syncytium formation. Syncytium formation occurs when the viral surface glycoprotein, gp120, expressed on the surface of HIV-infected cells binds to the viral receptor, CD4, on the surface of uninfected target cells (Lifson, et al., Science 232:1123-1127, 1986; Sodroski, et al., Nature 322:470-474, 1986). The viral transmembrane glycoprotein, gp41, and possibly additional cellular surface molecules (Kowalski, et al., Science 237:1351-1355, 1987; Hildreth, et al., Science 244:1075-1078, 1989) have been reported to mediate a membrane fusion process where one infected cell can fuse with multiple uninfected cells, the end result being the formation of multinucleated giant cells called syncytia L-tyrosine and L-dopa melanins were found to block syncytium formation and subsequent cytopathic effects when uninfected MT-2 cells were mixed with H9 cells chronically infected with HTLV-III$_B$, HTLV-III$_{RF}$, or HIV-2$_{ROD}$. The data is shown in Table C. As in infection assays (Table A), both melanins were less effective against HIV-2$_{ROD}$ than against the two HIV-1 isolates. Dopamine, serotonin, norepinephrine, L-dopa/glutathione, and L-dopa/L-cysteine melanins blocked syncytium formation between uninfected MT-2 cells and CEM cells chronically infected with HTLV-III$_B$ (Table C).

TABLE C*

| | μg/melanin ml | | | |
|---|---|---|---|---|
| Melanin (Virus) | 0.08 | 0.16 | 0.31 | 0.62 |
| L-tyrosine (IIIB) | — | 0 | 0 | 10 |

TABLE C*-continued

| | μg/melanin ml | | | |
|---|---|---|---|---|
| L-tyrosine (RF) | — | 0 | 0 | 0 |
| L-tyrosine (HIV-2) | — | 0 | 0 | 15 |
| L-Dopa (IIIB) | — | 0 | 0 | 0 |
| L-Dopa (RF) | — | 0 | 0 | 0 |
| L-Dopa (HIV-2) | — | 0 | 0 | 0 |
| Dopamine (IIIB) | 14 | 32 | 25 | 68 |
| Serotonin (IIIB) | 9 | 14 | 17 | 18 |
| Norepinephrine (IIIB) | 0 | 13 | 24 | 30 |
| L-Dopa/Glutathione (IIIB) | 0 | 10 | 10 | 16 |
| L-Dopa/L-Cysteine (IIIB) | 0 | 13 | 20 | 30 |
| Melanin (Virus) | 1.25 | 2.5 | 5 | 10 |
| L-tyrosine (IIIB) | 30 | 80 | 90 | 98 |
| L-tyrosine (RF) | 55 | 90 | 100 | 100 |
| L-tyrosine (HIV-2) | 25 | 43 | 70 | 80 |
| L-Dopa (IIIB) | 10 | 38 | 78 | 95 |
| L-Dopa (RF) | 60 | 82 | 100 | 97 |
| L-Dopa (HIV-2) | 5 | 22 | 38 | 70 |
| Dopamine (IIIB) | 74 | 100 | 88 | 78 |
| Serotonin (IIIB) | 39 | 40 | 83 | 95 |
| Norepinephrine (IIIB) | 39 | 68 | 60 | 58 |
| L-Dopa/Glutathione (IIIB) | 28 | 45 | 45 | 47 |
| L-Dopa/L-Cysteine (IIIB) | 53 | 96 | 100 | 91 |

*Values in this table are percent viable cell in anti-syncytial assays.

EXAMPLE V

Melanin Blockage of HIV-1 gp120 Binding to MT-2 Cells

Since gp-120-CD4 binding is an early event in HIV replication and is critical to syncytium formation, the fact that melanin blocked HIV early (Table B) and interfered with syncytium formation (Table C) suggests that gp120-CD4 interaction was affected. To investigate this possibility, purified HTLV-III$_B$ gp120 was allowed to bind to CD4 on the surface of MT-2 cells in the presence and absence of L-tyrosine and L-dopa melanins (10 μg/ml). Unbound gp120 was then removed by a series of washes after which bound gp120 was detected by flow cytometry. The fluorescence intensity of MT-2 cells was greatly decreased in the presence of both melanins. Compared to background fluorescence, L-tyrosine and L-dopa melanins reduced relative fluorescence intensities by 95% and 59%, respectively. These results indicate that melanin either blocked gp120 from binding to CD4 or decreased the avidity of binding allowing the gp120 to be washed off. When melanin was added after gp120 was allowed to bind, fluorescence intensity was similar to that seen in the absence of melanin. Therefore, the absence of gp120 detection was not simply due to melanin preventing antiserum from binding gp120.

EXAMPLE VI

Effect of Melanin on HIV-1 Reverse Transcriptase (RT) Activity

L-tyrosine and L-dopa melanins were examined for an ability to inhibit the viral RT in triton X-100-treated HTLV-III$_B$ lysates. Concentrations as high as b 50 μg/ml (which is notably brown) failed to inhibit the enzyme, a result which makes RT inhibition an unlikely mechanism for melanin's antiviral activity. Also, RT inhibition would require that melanin get into the cell. However, when MT-2 and H9 cells were incubated for 4 and 48 hours in the presence of L-tyrosine melanin at 10 μg/ml (a concentration which turns the medium light tan in color), no visual evidence of cell pigmentation was observed. Therefore, these cells do not appear capable of transporting and concentrating melanin from the medium.

EXAMPLE VII

Toxicity of L-dopa Melanin in Balb/c Laboratory Mice

The toxicity of L-dopa melanin was investigated in 10-12 week old, female Balb/c mice by giving them melanin in their drinking water or by intraperitoneal (i.p.) administration. In one set of experiments, 3 groups of 5 mice received melanin at 0, 1 or 10 mg/ml, respectively, in their drinking water for 5 days. All mice appeared healthy and normal and consumed equal amounts of water and food during this period. For the first 15 hours the mice were housed in metabolic chambers designed to collect urine and feces separately. Urine from mice that were fed melanin at 10 mg/ml was noticeably brown. This urine was filter-sterilized and found to be active against HIV-1 in MT-2 cells to a dilution of 1:200. The feces from this group was very black and, when dispersed in water, had an insoluble black product that was removed by centrifugation. This insoluble black substance could be solubilized by the addition of 0.1 N NaOH.

In another set of experiments, 3 groups of 4 mice received 100 μl intraperitoneal (i.p.) injections containing 0, 1 or 10 mg of melanin, respectively, per injection. The mice were observed for a period of 1 week. All mice receiving 0 and 1 mg doses appeared healthy throughout the test period. In contrast, two mice that received 10 mg of melanin died overnight and a third mouse died 2 days later. The fourth mouse in this group survived lethal toxicity. Therefore, the LD50 of L-dopa melanin in mice by intraperitoneal administration was determined to be between 1 and 10 g/kg.

I claim:

1. The method of treating a human patient infected with human immunodeficiency virus (HIV) which causes acquired immunodeficiency syndrome (AIDS), comprising administering to said patient water-soluble melanin, said melanin being administered by a route which introduces it into the blood in doses effective to inhibit the replication of HIV therein.

2. The method of claim 1 in which said water-soluble melanin is selected from the group consisting of melanins prepared by oxidation of L-dopa, L-dopa/cysteine, L-dopa/glutathione, L-tyrosine, serotonin, dopamine, adrenalin, and noradrenalin.

3. The method of claim 1 in which said water-soluble melanin is L-dopa melanin.

4. The method of claim 1 in which said water-soluble melanin is L-tyrosine melanin.

5. The method of claims 1, 2, 3, or 4 in which said patient is infected with HIV-1.

6. The method of claims 1, 2, 3, or 4 in which said patient is infected with HIV-2.

7. The method of treating a human patient infected with human immunodeficiency virus type 1 (HIV-1) which causes acquired immunodeficiency syndrome (AIDS), comprising orally administering to said patient water-soluble melanin in doses effective to inhibit the replication of HIV-1 in the patient's blood.

8. The method of treating a human patient infected with human immunodeficiency virus type 2 (HIV-2) which causes acquired immunodeficiency syndrome (AIDS), comprising orally administering to said patient water-soluble melanin in doses effective to inhibit the replication of HIV-2 in the patient's blood.

9. The method of treating a human patient infected with human immunodeficiency virus type 1 (HIV-1) which causes Acquired Immunodeficiency Syndrome (AIDS), comprising intravenously infusing into the blood of said patient water-soluble melanin in an amount effective to inhibit the replication of HIV-1 in the blood.

10. The method of treating a human patient infected with human immunodeficiency virus type 2 (HIV-2) which causes acquired immunodeficiency syndrome (AIDS), comprising intravenously infusing into the blood of said patient water-soluble melanin in an amount effective to inhibit the replication of HIV-2 in the blood.

11. The method of claims 7, 8, 9, or 10 in which said water-soluble melanin is orally administered or intravenously infused in an amount of from 5 to 50 milligrams per 24 hours.

12. The method of claims 7, 8, 9, or 10 in which said water-soluble melanin is selected from the group consisting of melanins prepared by oxidation of L-dopa, L-dopa/cysteine, L-dopa/glutathione, L-tyrosine, serotonin, dopamine, adrenalin, and noradrenalin.

13. The method of claims 7, 8, 9 or 10 in which said watersoluble melanin is L-dopa melanin.

14. The therapeutic use of water-soluble melanins for treatment of patients infected with human immunodeficiency virus (HIV).

* * * * *